(12) United States Patent
Fröjd et al.

(10) Patent No.: US 9,937,334 B2
(45) Date of Patent: *Apr. 10, 2018

(54) CATHETER WITH CUSTOMIZABLE CONNECTOR

(71) Applicant: ASTRA TECH AB, Mölndal (SE)

(72) Inventors: Göran Fröjd, Göteborg (SE); Marie-Josée Michon-Gente, Göteborg (SE)

(73) Assignee: ASTRA TECH AB, Mölndal (SE)

( * ) Notice: Subject to any disclaimer, the term of this patent is extended or adjusted under 35 U.S.C. 154(b) by 49 days.

This patent is subject to a terminal disclaimer.

(21) Appl. No.: 14/928,707

(22) Filed: Oct. 30, 2015

(65) Prior Publication Data

US 2016/0051802 A1 Feb. 25, 2016

Related U.S. Application Data

(63) Continuation of application No. 12/875,444, filed on Sep. 3, 2010, now Pat. No. 9,192,740.

(Continued)

(30) Foreign Application Priority Data

Sep. 4, 2009 (EP) .................................. 09169510

(51) Int. Cl.
*A61M 25/00* (2006.01)
*A61M 27/00* (2006.01)
(Continued)

(52) U.S. Cl.
CPC ...... *A61M 27/008* (2013.01); *A61M 25/0009* (2013.01); *A61M 25/0014* (2013.01);
(Continued)

(58) Field of Classification Search
CPC .......... A61M 25/0009; A61M 25/0017; A61M 25/0097; A61M 25/0111; A61M 25/0014;
(Continued)

(56) References Cited

U.S. PATENT DOCUMENTS 4,062,363 A 12/1977 Bonner, Jr.
4,547,194 A 10/1985 Moorehead
(Continued)

FOREIGN PATENT DOCUMENTS

CN 1326332 A 12/2001
DE 43 12 353 A1 11/1993
(Continued)

OTHER PUBLICATIONS

European Search Report dated Oct. 30, 2013; pp. 1-6.

*Primary Examiner* — Adam Marcetich
(74) *Attorney, Agent, or Firm* — Birch, Stewart, Kolasch & Birch, LLP

(57) ABSTRACT

A catheter, and preferably a urinary catheter, is disclosed, comprising an elongate shaft with a catheter insertion end and a flared connector connected to the elongated shaft opposite to the catheter insertion end. The flared connector forms a catheter connector end. Further, a gripping sleeve is fixedly connected to the flared connector, and arranged to enclose at least part of, and preferably essentially the whole, flared connector, apart from the catheter connector end. Hereby, a standard catheter can easily be customized for various use situations and users with different needs, in terms of e.g. gripping and manipulation possibilities. A method for producing such a customized catheter is also disclosed.

24 Claims, 3 Drawing Sheets

Related U.S. Application Data

(60) Provisional application No. 61/240,063, filed on Sep. 4, 2009.

(51) Int. Cl.
  *A61M 25/01* (2006.01)
  *B25G 1/00* (2006.01)
  *B25G 1/04* (2006.01)
  *A61M 25/06* (2006.01)

(52) U.S. Cl.
  CPC .... *A61M 25/0017* (2013.01); *A61M 25/0097* (2013.01); *A61M 25/0111* (2013.01); *A61M 2025/0046* (2013.01); *A61M 2025/0681* (2013.01); *B25G 1/00* (2013.01); *B25G 1/04* (2013.01); *Y10T 29/49826* (2015.01)

(58) Field of Classification Search
  CPC ........ A61M 27/008; A61M 2025/0046; A61M 2025/0681; B25G 1/04; B25G 1/00; Y10T 29/49826
  See application file for complete search history.

(56) References Cited

U.S. PATENT DOCUMENTS

| | | | |
|---|---|---|---|
| 5,505,710 A * | 4/1996 | Dorsey, III | A61M 1/008 604/158 |
| 5,797,882 A * | 8/1998 | Purdy | A61M 25/0023 604/164.09 |
| 5,800,399 A | 9/1998 | Bogert et al. | |
| 6,238,404 B1 | 5/2001 | Hidalgo et al. | |
| 6,260,890 B1 | 7/2001 | Mason | |
| 6,355,004 B1 * | 3/2002 | Pedersen | A61F 5/44 600/581 |
| 6,695,831 B1 | 2/2004 | Tsukada et al. | |
| 9,192,740 B2 * | 11/2015 | Frojd | A61M 25/0009 |
| 2002/0055722 A1 * | 5/2002 | Douglas | B29C 66/71 604/272 |
| 2004/0260327 A1 | 12/2004 | Mueller, Jr. et al. | |
| 2005/0033237 A1 * | 2/2005 | Fentress | A61M 25/0009 604/165.03 |
| 2005/0070882 A1 | 3/2005 | Mcbride | |
| 2005/0146136 A1 * | 7/2005 | Kawamura | A61M 39/10 285/255 |
| 2005/0187519 A1 | 8/2005 | Harris et al. | |
| 2006/0025753 A1 | 2/2006 | Kubalak et al. | |
| 2006/0127165 A1 * | 6/2006 | Vasek | A61M 25/0097 403/1 |
| 2006/0142737 A1 | 6/2006 | Tanghoj | |
| 2006/0178635 A1 | 8/2006 | Callaway | |
| 2006/0196783 A1 | 9/2006 | Bruun et al. | |
| 2006/0282150 A1 | 12/2006 | Olson et al. | |
| 2007/0066963 A1 | 3/2007 | Tanghoj | |
| 2008/0077176 A1 | 3/2008 | Hanlon et al. | |
| 2008/0172042 A1 | 7/2008 | House | |
| 2008/0260576 A1 | 10/2008 | Bruun et al. | |
| 2008/0275429 A1 * | 11/2008 | Sage | A61M 25/0014 604/536 |
| 2009/0054876 A1 | 2/2009 | Borodulin et al. | |
| 2009/0200187 A1 | 8/2009 | Nestenborg et al. | |
| 2009/0318746 A1 | 12/2009 | Thurmond, II et al. | |
| 2010/0087801 A1 | 4/2010 | Torstensen et al. | |
| 2010/0094216 A1 | 4/2010 | Yue et al. | |
| 2010/0106102 A1 * | 4/2010 | Ziebol | A61L 2/186 604/265 |
| 2010/0211050 A1 | 8/2010 | Luther | |

FOREIGN PATENT DOCUMENTS

| | | |
|---|---|---|
| DE | 201 05 899 U1 | 8/2001 |
| WO | WO 00/30575 A1 | 6/2000 |
| WO | WO 2004/050155 A1 | 6/2004 |
| WO | WO 2004/089454 A1 | 10/2004 |

* cited by examiner

CATHETER WITH CUSTOMIZABLE CONNECTOR

CROSS-REFERENCE TO RELATED APPLICATIONS

This application is a Continuation of copending application Ser. No. 12/875,444, filed on Sep. 3, 2010, which claims priority under 35 U.S.C. § 119(e) to U.S. Provisional Application No. 61/240,063, filed on Sep. 4, 2009, and under 35 U.S.C. § 119(a) to Application No. 09169510.6, filed in European Patent Office on Sep. 4, 2009, all of which are hereby expressly incorporated by reference into the present application.

TECHNICAL FIELD OF THE INVENTION

The present invention relates to a catheter, such as urinary catheters, and in particular to catheters of a relatively short length, such as female catheters.

BACKGROUND

The present invention relates to a catheter for draining bodily fluids, e.g. from the bladder. Urinary catheters are e.g. used by a large group of persons for intermittent catheterization, which is a daily-life procedure, taking place several times a day. Typically catheters for intermittent catheterization are used by patients suffering from urinary incontinence or by disabled individuals like para- or tetraplegics. Using an intermittent catheter, the bladder may be drained through a natural or artificial urethra. Many catheters for intermittent catheterization are provided with a hydrophilic coating or the like, providing a smooth and slippery surface for safe and comfortable insertion in the urinary canal.

To this end, catheters should preferably be designed to enable easy handling and introduction into the urethra, even for users having reduced dexterity. Further, in order to reduce the risk of e.g. urinary tract infections, the catheters should preferably be handled in a clean manner, without directly touching the insertable part of the catheter with the hands, in order to avoid contamination prior to use.

Catheters, such as urinary catheters, are normally produced in large volumes, having standardized lengths and standardized connector designs. However, it is sometimes requested to have large connector ends, in particular for short, female catheters, in order to improve maneuverability. However, provision of large assortment of different catheters, having different connector lengths, connector designs, catheter lengths, etc, makes the production costly. Typically catheters are designed for one-time use and accordingly the costs for producing, packing and sterilizing a catheter is an important issue. There is therefore a need for a simple and cost-effective way of modifying a pre-produced standard catheter to various specific needs, such as improved gripping possibilities.

An alternative approach to obtain improved usability of catheters is disclosed in US 2005/0070882, which discloses a urinary catheter with a cuff loosely arranged over the connector end. This loosely arranged cuff can be moved along the catheter, for use when handling the catheter. However, this approach requires a relatively skilled user, and is e.g. complicated to for users with reduced dexterity, and is also difficult to use with short catheters, such as female urinary catheters.

Further, US 2007/0066963 discloses a catheter assembly comprising a detachable catheter handle, which is connected to the rearward end of the catheter before use, in order to provide an enlarged handle for easier manipulation. Still further, US 2006/0142737 discloses a catheter assembly, including a catheter with a long connector end, for improved manipulation. However, both these prior art solutions are related to relatively complex catheter products, which are difficult and expensive to produce.

In other products the contamination problem of the handle portion has been addressed by providing a handle formed separately from the catheter for attachment to the catheter prior to the insertion. Unfortunately, handles which are separate from the catheter imply other problems both with respect to the manufacturing costs and with respect to handling of two separate components when attaching the handle to the catheter. In addition, separation of the catheter into two separate components implies an increased risk of contamination, in particular, if the handle part is reused. Furthermore, division of the catheter into a handle part separate from an insertable part does not solve the problems of complicated unpacking.

In conclusion there is still a need for catheters, which may be designed for simple and clean use, even for users with a reduced dexterity, and which can be produced in a cost-efficient manner.

SUMMARY OF THE INVENTION

It is therefore an object of the present invention to provide a catheter, and a method of producing such a catheter, which at least alleviates the above-discussed problems.

This object is obtained by means of a catheter and a method of producing in accordance with the appended claims.

According to a first aspect of the invention there is provided a catheter, and preferably a urinary catheter, comprising an elongate shaft with a catheter insertion end and a flared connector connected to the elongated shaft opposite to the catheter insertion end, the flared connector forming a catheter connector end; and a gripping sleeve being fixedly connected to said flared connector, and arranged to enclose at least a part of, and preferably essentially the whole, flared connector, apart from the catheter connector end.

By "fixedly connected" is in this context to understand a connection which is not intended to be opened during normal use. It does not necessarily mean that the fixedly connected parts may not be separated, but that the connection is strong enough to ensure that such separation does not occur during normal use. The fixed connection can be obtained in various ways, such as by friction fit, adhesion, mechanical interlocking and the like.

Hereby, it becomes possible to produce large series of catheters having standardized lengths and standardized flared connectors. The connector is preferably a relatively short conical connector part e.g. for connecting the catheter to elongate tubes or drainage containers for collecting urine. The connector also serves as a manipulation aid, and by gripping the connector, the catheter may be manipulated and inserted into the urinary canal (urethra).

Thus, the catheter without any gripping sleeve in itself is a catheter which is adequate for many use situations.

However, for customization, and simple production of other types of catheter products, the same, standard catheter may be used, and be completed with a gripping sleeve. Hereby, an extended and enlarged aggregate connector is provided. Such an enlarged gripping portion is highly advantageous in many situations, such as in products to be used by users with reduced dexterity, short catheters, where other types of insertion aids are difficult to use, etc. Thus, a catheter according to the present invention is particularly advantageous for short catheters, used e.g. by females, children or persons with an artificial urinary canal. In one embodiment of the invention the catheter is adapted to fit the female urethra, i.e. it may be provided in a length in the range of 50-200 mm, such as 130-180 mm, such as in a length in the size of 150 mm.

Further, the sleeve does preferably not extend past the rearward end of the catheter. Hereby, the ordinary handling of the catheter, e.g. connecting it to additional tubing or a urine collection bag, is not in any way affected.

By means of the present invention, it is possible to use the same production equipment for a large variety of different catheter products, which makes the production very cost-efficient. Further, it becomes possible to react quickly to market demands, and introduce specialized catheters for various types of specific use.

Preferably the gripping sleeve has an axial length significantly longer than the axial length of the flared connector. For example, the gripping sleeve may have an axial length which is at least 25% longer than the axial length of the flared connector, and preferably at least 50% longer. It is also preferred that the gripping sleeve has an axial length of at least 4 cm, and preferably at least 5 cm.

The catheter may be any type of catheter, but in a preferred embodiment the catheter is a urinary catheter.

The gripping sleeve is preferably connected to the flared connector end by means of a friction fit (i.e. press fit) or mechanical interlocking. This way of connecting the gripping sleeve makes the production very simple and cost-efficient. Alternatively or additionally, the gripping sleeve may be connected to the flared connector by means of at least one of welding and adhesion.

In order to further enhance the attachment of the gripping sleeve to the flared connector, the flared connector is preferably provided with an outwardly facing corrugation, and the gripping sleeve is preferably provided with a corresponding inwardly facing corrugation.

The outer surface of the gripping sleeve may be provided with various means for improve the gripping and handling. Thus, the gripping sleeve may be ergonomically shaped to make it easier to manipulate, especially for persons with reduced dexterity. For example, the gripping sleeve may be provided with an outwardly facing corrugation. The gripping sleeve may also be provided with outwardly protruding gripping means, such as wings. Other types of protruding parts, such as grooves, rugged surfaces, finger holes, etc, are also feasible.

The invention is particularly useful for hydrophilic catheters, i.e. catheters having a hydrophilic surface coating on part or the whole of the exterior surface of the elongate shaft.

Further, it is preferred that the flared connector comprises an outwardly protruding flange in the vicinity of the catheter connector end, said flange providing an abutment for the gripping sleeve. Hereby, the attachment of the gripping sleeve is improved, and further, it is ensured that the gripping sleeve does not protrude past the end of the flared connector.

According to a further aspect of the invention, there is provided a method of producing a customized catheter, and preferably a urinary catheter, comprising the steps of:

providing a base catheter comprising an elongate shaft and a flared connector with a catheter connector end connected to one end of said elongate shaft; and arranging a customizable gripping sleeve over said flared connector, to enclose at least a part of, and preferably essentially the whole, flared connector, apart from the catheter connector end, and fixedly connecting the gripping sleeve to said flared connector.

Hereby, similar advantages as discussed above with reference to the first aspect of the invention are obtained.

The method further preferably comprises the step of selecting a suitable gripping sleeve among a plurality of available gripping sleeves. Preferably, a plurality of different gripping sleeves are provided, and used on common base catheters to form a plurality of different catheters. Hereby, it becomes possible to provide a number of various gripping sleeve, corresponding to a number of different catheters, and to produce said different catheters in the same line of manufacturing.

These and other aspects of the invention will be apparent from and elucidated with reference to the embodiments described hereinafter.

BRIEF DESCRIPTION OF THE DRAWINGS

For exemplifying purposes, the invention will be described in closer detail in the following with reference to embodiments thereof illustrated in the attached drawings, wherein.

DESCRIPTION OF PREFERRED EMBODIMENTS

Figure 1:
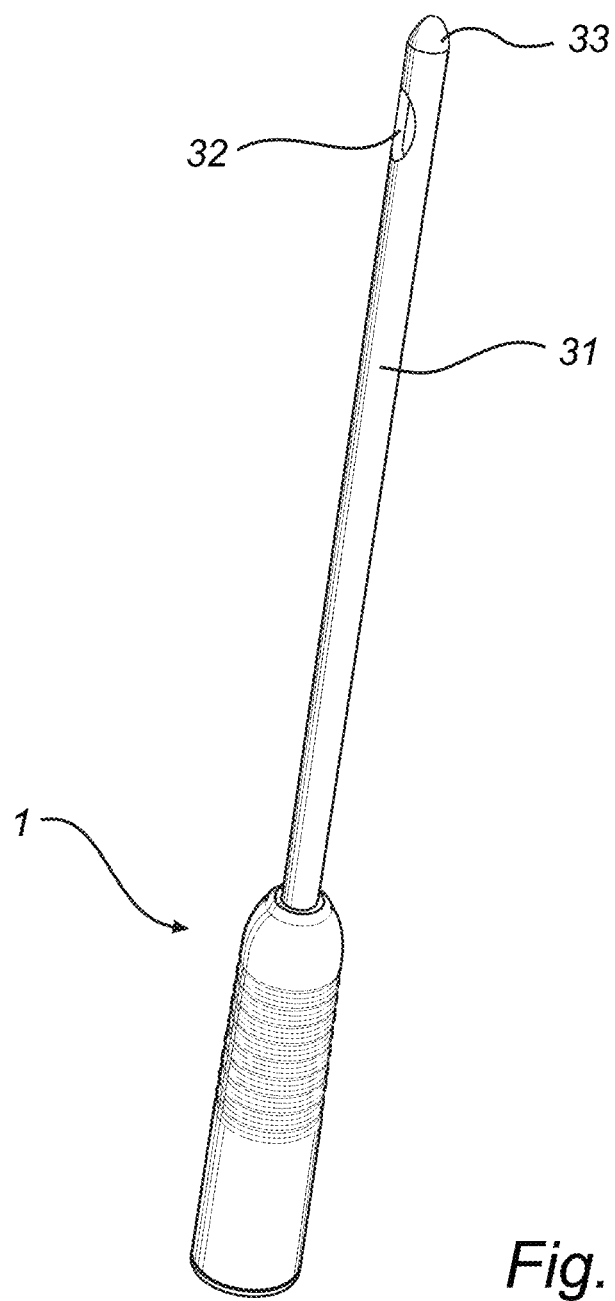
FIG. 1 illustrates a catheter in accordance with an embodiment of the present invention.
Figure 2:
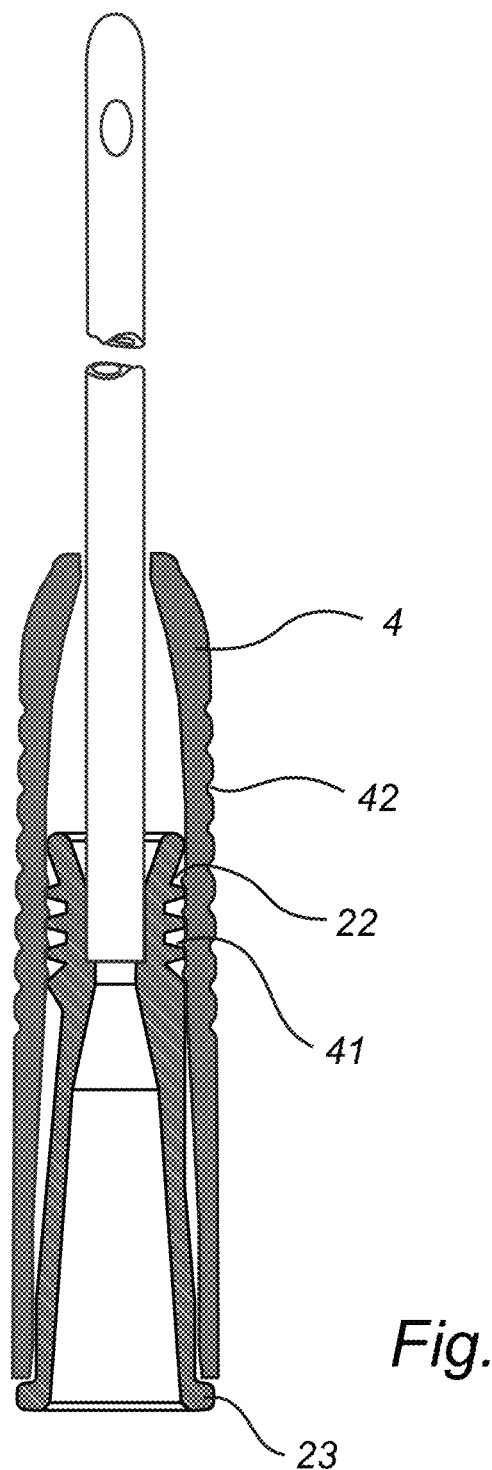
FIG. 2 illustrates a part of the catheter of FIG. 1, partially in section.

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations of the invention, e.g. the length of the catheter, etc.

Catheters may be used for many different purposes, and for insertion into various types of body-cavities. However, the following discussion is in particular concerned with the preferred field of use, hydrophilic urinary catheters, even though the invention is not limited to this particular type of catheters.

Figure 3:
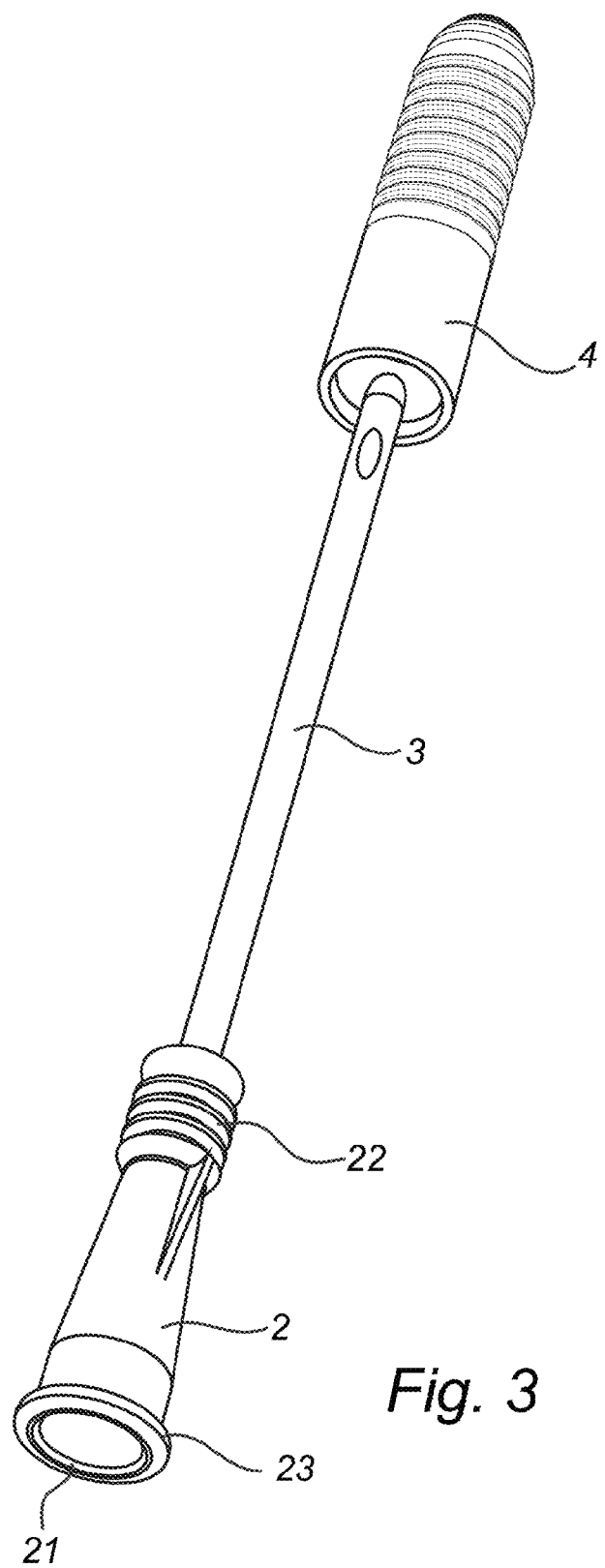
FIG. 3 illustrates an intermediate step in the assembly of the catheter of FIG. 1.

A catheter 1 as illustrated in the drawings, e.g. in FIG. 3, comprises a flared rearward portion, forming a flared connector 2, and an elongated shaft 3, connected to the flared connector 2, and in the opposite end having a catheter insertion end 31. The flared connector 2 forms a catheter connector end 21.

An open-ended internal lumen (not shown) extends from the catheter connector end 21 to a drainage aperture 32 in a rounded tip 33 of the elongate tube 3.

The flared connector 2 may function as a connector of the catheter 1, being connectable to other devices, such as a urine collection bag, a drainage tube or the like. It may have any size and form, forming a flared extension in relation to the elongate shaft, as is per se well known in the art. Further, the flared connector 2 may be connected to the elongate shaft 3 by means of welding, adhesion or the like, or form an integrated part of the elongate shaft.

At least a part of the elongate shaft 3 forms an insertable length to be inserted through a body opening of the user, such as the urethra in case of a urinary catheter. By insertable length is normally, in the context of a hydrophilic catheter, meant that length of the elongate shaft 3 which is coated with a hydrophilic material, for example PVP, and which is insertable into the urethra of the patient. Typically, this will be 50-140 mm for a female patient and 200-350 mm for a male patient. Even though PVP is the preferred hydrophilic material, other hydrophilic materials may be used, such as hydrophilic polymers selected from polyvinyl compounds, polysaccharides, polyurethanes, polyacrylates or copolymers of vinyl compounds and acrylates or anhydrides, especially polyethyleneoxide, polyvinyl-pyrrolidone, heparin, dextran, xanthan gum, polyvinyl alcohol, hydroxy propyl cellulose, methyl cellulose, copolymer of vinylpyrrolidone and hydroxy ethylmethyl acrylate or copolymer of polymethylvinyl ether and maleinic acid anyhydride. The coating may also comprise an osmolality-increasing compound, as is e.g. taught in EP 0 217 771

In addition, the catheter comprises a gripping sleeve 4 surrounding and being fixedly connected to the flared connector 2, and arranged to enclose essentially the whole flared connector, apart from the catheter connector end 21.

The gripping sleeve 4 preferably has an axial length significantly longer than the axial length of the flared connector 2.

The gripping sleeve is preferably connected to the flared connector end by means of a friction fit. Alternatively or additionally, the gripping sleeve may be connected to the flared connector by means of at least one of welding and adhesion. In order to further enhance the attachment of the gripping sleeve to the flared connector, the flared connector 2 is preferably provided with an outwardly facing corrugation 22, and the gripping sleeve 4 is preferably provided with a corresponding inwardly facing corrugation 41. Further, it is preferred that the flared connector 2 comprises an outwardly protruding flange 23 in the vicinity of the catheter connector end, providing an abutment for the gripping sleeve 4.

The gripping sleeve is a tubular part, with a first opening with an inward diameter preferably essentially corresponding with the corresponding external diameter of the flared connector, and a second opening with an inward diameter preferably corresponding with the corresponding external diameter of the elongate shaft. The gripping sleeve preferably has a cylindrical shape, and it could be circular or non-circular in a cross-sectional view.

The outer surface of the gripping sleeve 4 may be provided with various means for improve the gripping and handling. For example, the gripping sleeve may be provided with an outwardly facing corrugation 42. The gripping sleeve may also be provided with outwardly protruding gripping means, such as wings (not shown).

The catheter components can be made from a large number of feasible materials, as is per se well known in the art. The elongate shaft, the flared connector and the gripping sleeve may further be made of the same material, or by two or more different materials. In the latter case, the parts may be made from materials with different characteristics towards softness and/or rigidity. The gripping sleeve may e.g. be made from a low frictional material, or it may have a surface coating preventing sliding between the fingers of the user, or it may have a surface pattern facilitating a better grip. The gripping sleeve could be made from a material which is rigid compared to the insertable part of the catheter.

The various catheter parts, or at least a part of one or several of said parts, could be made from a thermoplastic elastomer or other thermoplastic materials, or from a curable elastomer material, or from any mixture or combination thereof. Thermoplastic elastomer materials may comprise materials like polyurethane elastomers, polyetherblockamide elastomers, polyester elastomers, polyolefin elastomers and polystyrene elastomers and SEBS. Other thermoplastic materials may comprise PVC, e.g. plasticized PVC, polyethylene homo- or co-polymers, polypropylene homo- or co-polymers, polyamide types, polyester types, fluorine-containing thermoplastic materials such as fluorine-containing elastomers among others. Curable elastomer material may comprise silicone elastomers and curable polyurethane elastomers among others. Latex rubbers and other rubbers are also feasible.

Each of the parts can be made e.g. by extrusion, injection moulding, blow moulding etc.

A method of manufacturing the above-discussed catheter preferably comprises the steps of first producing a base catheter comprising an elongate shaft and a flared connector with a catheter connector end connected to one end of said elongate shaft, as is per se known in the art. Subsequently, the gripping sleeve is arranged over the flared connector, to enclose essentially the whole flared connector, apart from the catheter connector end, and fixedly connecting the gripping sleeve to said flared connector. This is illustrated in FIG. 3.

The invention has now been described by means of preferred embodiments. However, many further variations are possible. For example, the griping sleeve may be attached to the flared connector in other ways, such as by means of mechanical interlocking, the gripping sleeve may be provided with various forms of external gripping means, etc. Such and other obvious modifications must be considered to be within the scope of the present invention, as it is defined by the appended claims. It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting to the claim. The word "comprising" does not exclude the presence of other elements or steps than those listed in the claim. The word "a" or "an" preceding an element does not exclude the presence of a plurality of such elements. Further, a single unit may perform the functions of several means recited in the claims.

The invention claimed is:

1. A urinary catheter, comprising:
   an elongate shaft with a catheter insertion end and a flared connector non-detachably connected to the elongated shaft opposite to the catheter insertion end, the flared connector forming a catheter connector end; and
   a gripping sleeve being fixedly connected to said flared connector so as not to be separable during normal use of the urinary catheter, and arranged to enclose at least part of the flared connector, apart from the catheter connector end,
   wherein the urinary catheter is configured and arranged to drain urine from a bladder, and wherein the gripping sleeve has an axial length longer than the axial length of the flared connector.

2. The catheter of claim 1, wherein the gripping sleeve has an axial length which is at least 25% longer than the axial length of the flared connector.

3. The catheter of claim 2, wherein the gripping sleeve has an axial length of at least 4 cm.

4. The catheter of claim 1, wherein the gripping sleeve has an axial length of at least 4 cm.

5. The catheter of claim 1, wherein the catheter is a urinary catheter, configured and arranged to drain urine from a bladder.

6. The catheter of claim 1, wherein the gripping sleeve is connected to the flared connector end by means of a friction fit or mechanical interlocking.

7. The catheter of claim 1, wherein the gripping sleeve is connected to the flared connector by means of at least one of welding and adhesion.

8. The catheter of claim 1, wherein the flared connector is provided with an outwardly facing corrugation, and wherein the gripping sleeve is provided with a corresponding inwardly facing corrugation.

9. The catheter of claim 1, wherein the gripping sleeve is provided with an outwardly facing corrugation.

10. The catheter of a claim 1, wherein the gripping sleeve is provided with outwardly protruding gripping members.

11. The catheter of claim 1, wherein the elongate shaft is provided with a hydrophilic surface coating.

12. The catheter of any claim 1, wherein the flared connector comprises an outwardly protruding flange in the vicinity of the catheter connector end, said flange providing an abutment for the gripping sleeve.

13. The catheter of a claim 1, wherein, the gripping sleeve is configured to enclose essentially the whole flared connector, apart from the catheter connector end.

14. The catheter of a claim 1, wherein the gripping sleeve is provided with outwardly protruding wings.

15. The catheter of claim 1, wherein the gripping sleeve has an axial length which is at least 50% longer than the axial length of the flared connector.

16. The catheter of claim 1, wherein the gripping sleeve has an axial length of at least 5 cm.

17. The catheter of claim 1, wherein the gripping sleeve has an axial length which is substantially smaller than an axial length of the elongate shaft.

18. The catheter of claim 1, wherein the gripping sleeve is made from a material which is rigid compared to an insertable part of the catheter.

19. The catheter of claim 1, wherein the flared connector is configured to attach to the elongate shaft during catheterization.

20. The urinary catheter of claim 1, wherein the flared connector and the gripping sleeve remain in position with respect to the elongate shaft before and during catheterization.

21. The catheter of claim 1, wherein the catheter insertion end is provided with a drainage aperture in a rounded tip.

22. A method of producing a customized urinary catheter, comprising the steps:
providing a base catheter comprising an elongate shaft with a catheter insertion end and a flared connector non-detachably connected to one end of said elongate shaft that is opposite to the catheter insertion end, the flared connector forming a catheter connector end; and
arranging a customizable gripping sleeve over said flared connector, to enclose at least a part of the flared connector, apart from the catheter connector end, and fixedly connecting the gripping sleeve to said flared connector so as not to be separable during normal use of the urinary catheter,
wherein the urinary catheter is configured and arranged to drain urine from a bladder, and wherein the gripping sleeve has an axial length longer than the axial length of the flared connector.

23. The method of claim 22, further comprising the step of selecting a suitable gripping sleeve among a plurality of available gripping sleeves.

24. The method of claim 22, wherein a plurality of different gripping sleeves are provided, and used on common base catheters to form a plurality of different catheters.

* * * * *